US006844188B1

(12) United States Patent
MacDonald et al.

(10) Patent No.: US 6,844,188 B1
(45) Date of Patent: Jan. 18, 2005

(54) METHODS AND MODIFIED CELLS FOR THE TREATMENT OF CANCER

(75) Inventors: Gene H. MacDonald, Chapel Hill, NC (US); Brian K. Martin, Durham, NC (US); Robert E. Johnston, Chapel Hill, NC (US); Jenny P.-Y. Ting, Chapel Hill, NC (US)

(73) Assignee: University of North Carolina at CHapel Hill, Chapell Hill, NC (US)

( * ) Notice: Subject to any disclaimer, the term of this patent is extended or adjusted under 35 U.S.C. 154(b) by 0 days.

(21) Appl. No.: 09/288,837

(22) Filed: Apr. 8, 1999

Related U.S. Application Data

(60) Provisional application No. 60/081,092, filed on Apr. 8, 1998.

(51) Int. Cl.[7] .................... C12N 15/86; C12N 15/09; C07H 21/04; A61K 39/00; A61K 48/00
(52) U.S. Cl. .................. 435/320.1; 435/69.3; 536/23.1; 536/23.5; 424/199.1; 424/277.1; 424/93.2; 424/93.6
(58) Field of Search ..................... 424/184.1, 185.1, 424/199.1, 93.1, 93.2, 93.3, 93.6, 277.1, 89, 207.1; 435/69.1, 69.3, 235.1, 236, 325, 320.1; 514/2, 21, 44; 536/23.1, 23.5, 23.7, 23.72, 24.1

(56) References Cited

U.S. PATENT DOCUMENTS

| | | | |
|---|---|---|---|
| 5,789,245 A | 8/1998 | Dubensky, Jr. et al. | 435/320.1 |
| 5,814,482 A | 9/1998 | Dubensky, Jr. et al. | 435/69.3 |
| 5,843,723 A | 12/1998 | Dubensky, Jr. et al. | 435/69.3 |
| 5,951,975 A | 9/1999 | Falo, Jr. et al. | 424/93.2 |
| 6,015,694 A | 1/2000 | Dubensky, Jr. et al. | 435/69.3 |
| 6,468,982 B1 * | 10/2002 | Weiner et al. | 514/44 |

FOREIGN PATENT DOCUMENTS

| | | | |
|---|---|---|---|
| WO | WO/95/07994 | * 3/1995 | |
| WO | WO 95/07994 | 3/1995 | C12N/15/86 |
| WO | WO 95/32733 | 12/1995 | A61K/39/193 |
| WO | WO 96/17072 | 6/1996 | C12N/15/86 |
| WO | WO 96/21416 | 7/1996 | C12N/15/86 |
| WO | WO 97/24447 | 7/1997 | C12N/15/63 |
| WO | WO 98/00163 | 1/1998 | A61K/39/00 |
| WO | WO 99/30734 | 6/1999 | A61K/39/00 |
| WO | WO 00/39318 | 7/2000 | C12N/15/86 |
| WO | WO 92/10578 | 6/2002 | C12N/15/86 |

OTHER PUBLICATIONS

Caley et al., Journal of Virology, vol. 71 No 4, pp. 3031–3038 (1997).*
Gardner et al., Journal of Virology, vol. 74 No 24, pp. 11849–11857 (2000).*
Disis et al., Journal of Immunology, vol. 156, pp. 3151–3158 (1996).*
Davis et al., Vaccines 95:387–391, 1995.*
Davis et al., Journal of Virology, 70(6):3781–3787, 1996.*
DeVeerman et al.; *Retrovirally Transduced Bone Marrow–Derived Dendritic Cells Require CD4+T Cell Help to Elicit Protective and Therapeutic Antitumor Immunity*, The Journal of Immunology 162:144–151 (1999).
Dietz et al.; *High Efficiency Adenovirus–Mediated Gene Transfer to Human Dendritic Cells*, Blood, 91:2 392–398 (1998).
Galili et al.; *Natural anti–Gal antibody as a universal augmenter of autologous tumor vaccine immunogenicity*, Immunology Today 18:6 281–285 (1997).
Ikonomidis et al.; *Influenza–specific immunity induced by recombinant Listeria monocytogenes vaccines*, Vaccine 15:4 433–440 (1997).
Kawakami et al.; Section 3.1 *Genes Coding for Tumor Antigens Recognized by T Lymphocytes*, Biologic Therapy of Cancer Second Edition, J.B. Lippincott Company, 1995 pp. 53–63.
Pan et al.; *A recombinant Listeria monocytogenes vaccine expressing a model tumour antigen protects mice against lethal tumour cell challenge and causes regression of established tumours*, Nature Medicine 1:5 471–477 (1995).
Pan et al.; *Regression of Established Tumors in Mice Mediated by the Oral Administration of a Recombinant Listeria monocytogenes Vaccine*[1], Cancer Research 55:4776–4779 (1995).
Restifo; *The new vaccines: building viruses that elicit antitumor immunity*, Current Opinion in Immunology, 9:658–663 (1997).
Restifo et al.; *Transfectant Influenza A Viruses Are Effective Recombinant Immunogens in the Treatment of Experimental Cancer*, Virology 249:89–97 (1998).
Rosenberg; *A New Era for Cancer Immunotherapy Based on the Genes that Encode Cancer Antigens*, Immunity 10:281–287 (1999).

(List continued on next page.)

*Primary Examiner*—James Housel
*Assistant Examiner*—Zachariah Lucas
(74) *Attorney, Agent, or Firm*—Myers, Bigel, Sibley & Sajovec, P.A.

(57) ABSTRACT

The present invention provides methods of preventing and/or treating cancers (including tumors). In one preferred embodiment, the invention is practiced to induce regression of an existing cancer or tumor and/or to prevent metastasis and/or to prevent growth of metastatic nodules. In other preferred embodiments, the invention may be used as a prophylaxis to prevent the development of primary cancers through a childhood or adult vaccination program against specific tumor antigens for cancers with high incidences. In an alternate preferred embodiment, the present invention provides methods of establishing an immune response against a universal artificial tumor antigen through a childhood or adult vaccine program, thus providing a long-term immune response that can be utilized at any point to treat any cancer which develops later in life. The present invention also provides cancer and tumor cells stably expressing an artificial antigen, preferably an artificial cell-surface antigen.

6 Claims, 6 Drawing Sheets

OTHER PUBLICATIONS

Schuler et al.; *Dendritic Cells as Adjuvants for Immune–mediated Resistance to Tumors*, J. Exp. Med. 186:8 1183–1187 (1997).

Song et al.; *Antigen presentation in retroviral vector–mediated gene transfer in vivo*, Proc. Natl. Acad. Sci. USA 94:1943–1948 (1997).

Song et al.; *Dendritic Cells Genetically Modified with an Adenovirus Vector Encoding the cDNA for a Model Antigen Induce Protective and Therapeutic Antitumor Immunity*, J. Exp. Med. 186:8 1247–1256 (1997).

Specht et al.; *Dendritic Cells Retrovirally Transduced with a Model Antigen Gene Are Therapeutically Effective against Established Pulmonary Metastases*, J. Exp. Med. 186:8 1213–1221 (1997).

Storkus et al.; Section 3.2 *Tumor Antigens Recognized by Immune Cells*, Biologic Therapy of Cancer Second Edition, J.B. Lippincott Company, 1995 pp. 64–77.

Wang et al.; *Active Immunotherapy of Cancer with a Non-replicating Recombinant Fowlpox Virus Encoding a Model Tumor Associated Antigen*, The Journal of Immunology 154:4685–4692 (1995).

Wu et al.; *Tolerance to a Dominant T Cell Epitope in the Acetylcholine Receptor Molecule Induces Epitope Spread and Suppresses Murine Myasthenia Gravis*[1], The Journal of Immunology 159:6 3016–3023 (1997).

Pushko et al.; *Replicon–Helper Systems from Attenuated Venezuelan Equine Encephalitis Virus: Expression of Heterologous Genes in Vitro and Immunization against Heterologous Pathogens in Vivo*, Virology 239:389–401 (1997).

International Search Report, PCT/US99/07704, Date of Mailing: Dec. 15, 1999.

Johnston, "Alphavirus Expression Vectors: Potential Applications for Gene Expression, Vaccines and Gene Therapy," a list of slides, *Presentation to the Scientific Advisory Board of OraVax, Inc.* Boston, MA (Mar. 31, 1997).

\* cited by examiner

METHODS AND MODIFIED CELLS FOR THE TREATMENT OF CANCER

RELATED APPLICATION INFORMATION

This application claims the benefit of U.S. Provisional Application No. 60/081,092 filed Apr. 8, 1998, which is incorporated by reference herein in its entirety.

FEDERAL SUPPORT

The present invention was made with government support under grant number DAMD17-94-J-4430 from the United States Army Research and Development Command, grant number F32-A109778 from the National Institute of Health, grant number A141580 from the National Institute of Health, and grant number DAMD17-97-1-7142 from the Department of Defense. The government has certain rights to this invention.

FIELD OF THE INVENTION

The present invention relates to methods and compositions for the prevention and treatment of cancer, more particularly, immunological methods and compositions for the prevention and treatment of cancer.

BACKGROUND OF THE INVENTION

Attenuated, live virus vaccines are recognized as one of the most potent approaches to stimulating a protective immune response to pathogens and have been employed with success in the prevention of infectious diseases. Live virus vaccine vectors utilize the same advantages, stimulating both cytolytic T lymphocyte (CTL) activity and antibody production, without the danger of revertent virulent virus. Venezuelan equine encephalitis virus (VEE) derived vaccine vectors expressing heterologous genes have been developed with success in murine and primate models to protect against challenge with influenza virus (N. L. Davis et al., (1996) *J. Virol.* 70:3781–7), simian immunodeficiency virus (SIV; N. L. Davis et al., (1999) *Proc. Natl. Acad. Sci. USA*, submitted) and Marburg virus (M. Hevey et al., (1998) *Virology* 251:28–37).

In addition, live virus, non-propagating VEE replicon particles (VRP), expressing heterologous antigens, successfully protect against a lethal challenge of influenza in mice (P. Pushko et al., (1997) *Virology* 239:389–401) and SIV in primates (N. L. Davis et al., (1999) *Proc. Natl. Acad. Sci. USA*, submitted).

The goal of tumor immunotherapy is to induce a strong immune response against metastatic or residual disease. One of the most promising protocols in tumor immunotherapy is the use of ex vivo expanded dendritic cells (DC). Monocytes are isolated from peripheral blood then expanded and differentiated using cytokines and differential adhesion (reviewed in E. Gilboa et al., (1998) *Cancer Immunol. Immunother,* 46:82–7). These cells are modified via various protocols to present tumor antigens, and then the DC are infused back into the patient. DC are believed to target to the lymph nodes where they stimulate T cell immunity by interaction of the T cell receptor (TCR) of the T cell and class II and/or class I major histocompatability complex (MHC) of the DC.

These protocols, however, present several difficulties. First, large numbers of monocytes can be difficult to obtain from cancer patients due to an overall immunodepressed state. In addition, the ex vivo differentiation of the cells is time consuming and expensive and foreign proteins from the in vitro cultures can complicate the resulting immune response.

Given these drawbacks, there is a need in the art for alternative protocols for presenting tumor antigens in vivo to induce a host immune response thereto.

SUMMARY OF THE INVENTION

The present invention provides methods of preventing and/or treating cancers (including tumors-forming cancers). In particular preferred embodiments, the invention is practiced to induce regression of an existing cancer or tumor and/or to prevent metastasis and/or growth of metastatic nodules. In other preferred embodiments, the invention may be used as a prophylaxis to prevent the development of primary cancers through a childhood or adult vaccination-program against specific cancer antigens. In alternate preferred embodiments, the present invention provides methods of establishing an immune response against a universal artificial tumor antigen through a childhood or adult vaccine program, thus providing a long-term immune response that can be utilized at any point to treat any cancer which develops later in life. According to this embodiment, vaccination may be before or after the development of cancer. The present invention also provides cancer and tumor cells stably expressing an artificial antigen, preferably an artificial cell-surface antigen.

An alphavirus-based vaccine vector offers several advantages over other live virus vector delivery systems such as adenovirus and poliovirus. Venezuelan Equine Encephalitis virus (VEE) has been shown to primarily target dendritic cells following a subcutaneous inoculation. Targeting of antigen-presenting cells and the concentration of infecting virus directly within the lymph nodes may be responsible for the strong immunogenic nature of VEE based vectors and vaccines. The use of non-propagating alphavirus replicon particle vectors provides additional advantages and vastly increases the safety of using live virus, both by restricting viral spread and possible virulence. These features can be further enhanced by the use of alphavirus vectors containing attenuating mutations in the nonstructural or structural proteins. Finally, pre-existing immunity to VEE is minimal in the human population in contrast to adenovirus and poliovirus. Different alphavirus vectors can be used, if necessary, to prevent the development of an interfering immune response and to allow for multiple vaccinations.

The present invention provides a composition comprising infectious alphavirus particles in an immunogenic effective amount, wherein the alphavirus particles comprise one or more heterologous nucleotide sequences each encoding an antigen, and wherein the antigen is a native cancer cell antigen or an artificial cancer antigen (i.e., an antigen that is not normally expressed by the cancer cell). Also provided are pharmaceutical formations comprising the inventive compositions of infectious alphavirus particles.

As a further aspect, the present invention provides a kit for modifying a mammalian cell, comprising: (a) assay components for determining the pre-existing immunity of a subject afflicted with cancer to one or more antigens; and (b) one or more vectors suitable for introducing and expressing an antigen in a mammalian cell, where each of the vectors comprises one or more heterologous nucleotide sequence(s) encoding an antigen from the one or more antigens.

As a further aspect, the present invention provides a method for inducing a protective immune response in a subject afflicted with cancer, comprising: (a) modifying a cell to express one or more antigens against which the subject has a pre-existing immunity; and (b) introducing the modified cell into the subject, wherein the modified cell elicits an immune response against the subject's cancer.

Also provided is a method for inducing a protective immune response in a subject afflicted with cancer, comprising: (a) screening a subject afflicted with cancer for pre-existing immunity against one or more antigens; (b) selecting one or more antigens against which the subject demonstrates immunity; (c) modifying a cell to express the one or more selected antigens; and (d) introducing the modified cell into the subject, wherein the modified cell elicits an immune response against the subject's cancer.

As a further aspect of the invention is a method for inducing a protective immune response against cancer in a subject, comprising: (a) immunizing a subject against one or more antigens prior to the detection of cancer in the subject; (b) modifying a cell to express the one or more antigens of (a); and (c) introducing the modified cell into the subject, wherein the modified cell elicits an immune response against the subject's cancer.

A still further aspect of the invention is a method for inducing a protective immune response against cancer in a subject, comprising immunizing a subject against an antigen prior to the detection of cancer in the subject, wherein the immunizing step is carried out using an alphavirus vector comprising a nucleotide sequence encoding the antigen.

As a further aspect, the present invention provides a method for inducing a protective immune response against cancer in a subject, comprising: (a) immunizing a subject afflicted with cancer against one or more antigens; (b) modifying a cell to express the one or more antigens of (a); and (c) introducing the modified cell into the subject, wherein the modified cell elicits an immune response against the subject's cancer.

A yet further aspect of the invention is a method for inducing a protective immune response against cancer, comprising the step of immunizing a subject against a native cancer antigen, wherein the immunizing step is carried out using an alphavirus vector comprising a nucleotide sequence encoding a native cancer antigen.

As a further aspect, the present invention provides a method for inducing an immune response against a native cancer antigen, comprising the step of immunizing a subject afflicted with cancer against an antigen native to the subject's cancer, wherein the immunizing step is carried out using an alphavirus vector comprising a nucleotide sequence encoding an antigen native to the subject's cancer.

These and other aspects of the present invention are set forth in more detail in the description of the invention below.

BRIEF DESCRIPTION OF THE DRAWINGS

FIGS. 1A and 1B are a graphical representation of the results of a study demonstrating that VRP-HA vaccination inhibits tumor growth. Panel A. Tumor incidence as detected by palpation (VRP-HA; black, VRP-M/C; white, Mock; grey). Panel B. Tumor growth over time (VRP-HA; ▮, VRP-M/C; ■, Mock; ●). Three groups of 8 BALB/C 7–8 week old female mice were inoculated with either $5\times10^5$ infectious units (IU) of either V3014-HA VRP, V3014-M/C VRP or diluent (mock; phosphate buffered saline with 1% donor calf serum), subcutaneously in the left rear footpad. Mice were boosted three weeks later by the same protocol, and three weeks later were inoculated intramuscularly (im) in the left calf with $10^3$ LINE 1-HA tumor cells. Tumor establishment was detected by palpation (Panel A) and growth was determined by the average of two caliper measurements of the right calf (Panel B). Animals were sacrificed when the tumor diameter exceeded 0.5 inches.

FIG. 2 is a graphical representation of VRP-HA induced tumor regression. At day 31 post LINE1-HA inoculation (marked by arrow), seven mice from the negative control groups (diluent, triangle; VRP-M/C, circles) with tumors from 0.20–0.3 inches in diameter were inoculated with $10^6$ IU of VRP-HA subcutaneously in the left rear foot pad and measured for tumor growth.

FIG. 3 is a graphical representation of the effects of immunity to LINE1-HA tumors on LINE1 tumor growth. Eight mice from the group pre-immunized with VRP-HA before LINE1-HA inoculation (squares) and which never developed tumors, two mice from the negative control group whose tumors regressed after receiving VRP-HA (triangles), and four naive mice which had never been immunized with either VRP-HA or LINE1-HA (circles) were injected on day 48 im with $10^3$ LINE1 tumor cells in either the left (designated L) or right calf (designated R) and tumor growth was monitored.

FIGS. 5A–5C are a graphical representation of the results of a study demonstrating that $CD8^+T$ lymphocytes confer protection against LINE1-HA tumor growth. Splenocytes were purified from mice which had been immunized with either VRP-HA or VRP-M/C, as above, with an additional boost three weeks following the second boost. $CD4^+$ and $CD8^+$ lymphocytes were sequentially positively selected using MACS $VS^+$ magnetic columns (Miltenyi Biotec). The cells in the flow-through sample were considered to be enriched for B lymphocytes. Lymphocyte subsets from two mice were pooled and inoculated intravenously (iv) in the tail of a naive recipient, and 48 hours later the mice were challenged with LINE1-HA tumor cells. Mice were individually monitored for tumor growth with four mice per group. Closed squares represent cells transferred from VRP-M/C vaccinated mice; closed diamonds represent cells transferred from VRP-HA vaccinated mice. Panel A, CD8+ T cell transfer; Panel B, CD4+ T cell transfer; Panel C, flow through (B cell enriched).

DETAILED DESCRIPTION OF THE INVENTION

The present invention provides a general approach to the prevention and treatment of cancers (including tumor-forming cancers) using immunological techniques. Unlike previous attempts to immunize animals against tumor or cancer cells, the present invention does not depend on identifying and characterizing specific native (i.e., naturally-occurring) cancer antigens. By the terms "treating cancer" or "treatment of cancer", it is intended that the severity of the cancer is reduced or the cancer is at least partially eliminated. Alternatively, these terms are intended to mean that metastasis of the cancer is reduced or at least partially eliminated. As a further alternative, these terms indicate that growth of metastatic nodules (e.g., after surgical removal of a primary tumor) is reduced or at least partially eliminated.

By the terms "prevention of cancer" or "preventing cancer" it is intended that the inventive methods at least partially eliminate or reduce the incidence or onset of cancer. Alternatively stated, the present methods slow, control, decrease the likelihood or probability, or delay the onset of cancer in the subject.

The invention is based, in part, on the discovery that cancers can both be prevented and treated by immunizing against an artificial cancer cell antigen. An "artificial cancer cell antigen" or an "artificial tumor antigen" is an antigenic molecule that is not normally found in the cancer or tumor cells, but can be expressed therein and induce an immune response. For example, the antigenic molecule may be an infectious disease antigen. As used herein, artificial cancer cell antigens include artificial tumor antigens. Genetic engineering techniques are employed to express the antigenic molecule in cancer or tumor cells, respectively. Preferably, the antigenic molecule is a protein or peptide, more preferably, a cell-surface protein or peptide.

Artificial cancer cell antigen(s) can be any suitable antigenic protein that induces an active immune response against the antigen. Additionally, when administered according to the present invention, the artificial cancer cell antigen should be able to induce an active and protective immune response against unmodified cancer cells. As will be appreciated by those skilled in the art, it is preferred that the artificial cancer cell antigen does not induce an immune response against non-cancer host cells, i.e., cause an autoimmune response. Preferably, the artificial cancer antigen is an infectious disease antigen, as described above. Also preferred are cell-surface antigens, more preferably cell surface proteins or peptides. The antigen may be expressed on the cell surface by any means known in the art, for example, by insertion into the cellular membrane or by presentation on the cell surface, e.g., by MHC molecules. Alternatively, an engineered antigen can be designed for use in a vaccination program based on known strongly-immunogenic epitopes. Such designer antigens may include one or more known epitopes, including but not limited to, helper T cell epitopes, cytotoxic T cells epitopes, T-dependent B cell epitopes, T-independent B cell epitopes, and the like. As a further alternative, a subject can be vaccinated with a "cocktail" of engineered antigens, containing multiple epitopes. As a further alternative, antigens can be engineered to be compatible with the various known HLA haplotypes. Individual subjects can be screened for their HLA type and then vaccinated with the appropriate HLA-specific antigen or antigens.

The present invention is advantageously carried out by immunizing the subject with an alphavirus vector, more preferably, an alphavirus replicon particle vector (as described hereinbelow). Also preferred are Venezuelan Equine Encephalitis (VEE) virus vectors and replicon particle vectors. While not wishing to be held to any particular theory of the invention, it appears that the strong immunogenic response elicited in response to alphavirus, more particularly VEE, vectors is a result of alphavirus infection of dendritic cells, (i.e., antigen-presenting cells). Moreover, the alphavirus 26S subgenomic promoter, more particularly the VEE 26S promoter, is a strong promoter that appears to be highly expressed in dendritic cells. The effectiveness of alphavirus vaccines may be attributable, at least in part, to high level expression of antigen driven by the 26S subgenomic promoter.

Cancer or tumor cells may be removed from a cancer patient who has previously been vaccinated against an artificial cancer cell antigen, the cancer cells modified to express the artificial antigen, and then re-introduced into the patient. An active immune response will be mounted against the artificial antigen expressed by the modified cancer cells. There will also be an active immune response against native (i.e., naturally-occurring) cancer cell antigens. While not wishing to be held to any particular theory of the invention, it appears that this immune response to native cancer cell antigens is induced by the process of epitope spread, as this term is understood in the art (see, e.g., B. Wu et al., (1997) *J. Immunol.* 159:3016). Thus, the present invention provides a universal antigen, i.e., an antigen that can be used to elicit an active immune response against any cancer, independent of the specific native cancer cell antigens present. Typically, the universal antigen is an antigen that is not expressed by cancer cells or the particular cancer to be treated and/or prevented. Preferably, the universal antigen is a cell-surface protein or peptide.

In alternative embodiments of the invention, the cancer cells are removed from a donor subject, modified, and then introduced into a recipient subject or subjects. The cell recipient subject may be the same or a different subject than the donor subject. It is preferred that the patient's own cancer cells be modified and re-introduced back into the patient. If the donor and recipient subjects are different, the donated cancer cells and the cancer cells of the recipient preferably share at least one native antigen. In addition, the modified cancer cells are preferably HLA compatible with the recipient.

As a further alternative, it is possible to practice the present invention with cells that are not cancer cells. Typically, according to this embodiment, the patient's cancer cells and the modified cells will share at least one antigen native to the patient's cancer cells. In this manner, introduction of the modified cells expressing the artificial cancer cell antigen and the native cancer cell antigen will induce an immune response against the patient's cancer cells.

Typically, cancer cells will be removed from the cell donor patient, manipulated ex vivo, and then introduced into the cell recipient patient. In alternate embodiments, it is possible to use the present invention with cultured cancer or stored cancer cells that have been modified to express the artificial cancer cell antigen of interest. The stock of cultured or stored cancer cells are preferably HLA compatible with the patient's HLA type. Such cells can be introduced into patients afflicted with the same type of cancer to elicit a protective immune response against the cancer. For example, stock preparations of breast cancer cells expressing the HER2 or BRCA1 genes and an artificial cancer cell antigen are useful to treat women who have HER2-induced or BRCA1-induced breast cancers, respectively, and who are vaccinated against the artificial cancer cell antigen. The recipient's cancer cells and the stock cancer cells may share any antigen (e.g., a native cancer antigen). According to this embodiment, the cancers need not be of the same origin or type. Moreover, the donor cells need not be cancer cells at all, as long as the donor cells express at least one antigen expressed by the recipient's cancer cells (e.g., a native cancer cell antigen).

The invention is also useful to create an anti-cancer immune response prior to the development of cancer by a combination of vaccination and cancer cell modification. Alternatively, the invention can be employed to take advantage of a cancer patient's pre-existing immune responses by directing these pre-existing immune responses against genetically-modified cancer cells.

The approach disclosed herein provides a generalized strategy for treating and preventing cancers of any origin, either tumor forming or non-tumor forming cancers. The inventive methods can be used to treat both the primary cancer and to prevent metastasis. Alternatively, the inventive methods can be advantageously employed to reduce or prevent growth of metastatic nodules (e.g., following surgical removal of a primary tumor). The term "cancer" has its understood meaning in the art, for example, an uncontrolled growth of tissue that has the potential to spread to distant sites of the body (i.e., metastasize). Exemplary cancers include, but are not limited to, leukemias, lymphomas, colon cancer, renal cancer, liver cancer, breast cancer, lung cancer, prostate cancer, ovarian cancer, melanoma, and the like. Preferred are methods of treating and preventing tumor-forming cancers. The term "tumor" is also understood in the art, for example, as an abnormal mass of undifferentiated cells within a multicellular organism. Tumors can be malignant or benign. Preferably, the inventive methods disclosed herein are used to prevent and treat malignant tumors.

Methods of introducing and expressing the artificial antigen in the cancer cell can be accomplished by any suitable method and with any suitable vector known in the art. Viral vectors are preferred, with retroviral and alphavirus vectors being more preferred. Preferably, modified cancer cells are γ-irradiated prior to introduction into the patient. Irradiated cells will continue to produce antigenic protein for a period following irradiation, but will be unable to replicate in recipient patients. Typically, a patient will be injected with $10^5$ to $10^9$, and more preferably $10^6$ to $10^8$ modified cells. The method and site of introduction of the modified cells is not critical, although if the cancer is a solid tumor, introduction of the modified cells near the site of the tumor is preferred. Cells can be introduced by any suitable route of administration, with parenteral routes (e.g., subcutaneous, intracerebral, intradermal, intramuscular, intravenous, intraarticular) being preferred, and intramuscular injection being most preferred.

The present invention is suitable for both medical and veterinary uses. Suitable subjects include, but are not limited to, mammalian and avian subjects, preferably, mammalian subjects, more preferably human, simian, porcine, bovine, caprine, equine, feline, ovine, canine, chicken and turkey subjects, most preferably human subjects.

An "active immune response" or "active immunity" is characterized by "participation of host tissues and cells after an encounter with the immunogen. It involves differentiation and proliferation of immunocompetent cells in lymphoreticular tissues, which lead to synthesis of antibody or the development cell-mediated reactivity, or both." Herbert B. Herscowitz, *Immunophysiology: Cell Function and Cellular Interactions in Antibody Formation*, in IMMUNOLOGY: BASIC PROCESSES 117 (Joseph A. Bellanti ed., 1985). Alternatively stated, an active immune response is mounted by the host after exposure to immunogens by infection or by vaccination. Active immunity can be contrasted with passive immunity, which is acquired through the "transfer of preformed substances (antibody, transfer factor, thymic graft, interleukin-2) from an actively immunized host to a non-immune host." *Id.*

The terms "protective" immune response or "protective" immunity against cancer or tumor cells, as used herein, are intended to mean that the host mounts an active immune response against cancer or tumor cells, respectively. While not wishing to be bound by any particular theory of the invention, typically the protective immune response or protective immunity will arise when the host mounts an active immune response to native cancer antigens as well as to the artificial cancer cell antigen. A protective immune response is one that is beneficial to the host in that it prevents or reduces the incidence of cancer and/or is useful in the treatment of cancer, for example, by causing regression of the cancer and/or by preventing metastasis and/or by preventing growth of mestastatic nodules. Such protective effects may be complete or partial, as long as the benefits of the treatment outweigh any disadvantages thereof.

The terms "vaccination" or "immunization" are well-understood in the art. For example, the terms vaccination or immunization can be understood to be a process that increases an organism's immune reaction to antigen and therefore to resist or overcome infection. In the case of the present invention, vaccination or immunization against artificial or native cancer cell antigens will increase the organism's immune response and resistance to invasion by cancer cells.

A. The Use of Pre-Existing Immune Responses in the Treatment or Prevention of Cancer.

This embodiment of the invention is based on the manipulation of a preexisting immune response, typically active, to an immunogen. The pre-existing immune response can be a result of vaccination (e.g., childhood vaccination) or natural exposure. According to this embodiment, individual cancer patients are screened for their particular immune responses to a panel of common infectious disease antigens or other wide-spread antigens. An antigen(s) is chosen from the panel to which the patient already shows a relatively strong immune response. Preferably, an antigen(s) is chosen to which the patient shows a comprehensive (i.e., both cellular and humoral) immune response.

In particular preferred embodiments, cancer cells are then removed from the cancer patient (as described above) and genetically modified to express the selected antigen(s). The modified cancer cells, expressing the artificial cancer cell antigen(s) are then re-introduced into the patient. Alternatively, the modified cells can be from another donor, from a stock of stored cells, or from cultured cells, each as described hereinabove. Preferably, the artificial cancer cell antigen(s) is a cell-surface protein or peptide. The patient's pre-existing immunity against the expressed antigen(s) will be directed against the artificial cancer cell antigen(s) expressed by the modified cancer cells. In addition, an immune response will be elicited against native (i.e., naturally-occurring) tumor antigens, typically as a result of epitope spread. This cross-priming reaction against the native tumor antigens will result in an active and protective immune response against unmodified cancer cells as well.

Accordingly, this embodiment of the invention provides a method of treating existing cancers. In particular, the present invention provides a method of treating existing tumors by causing the regression of the tumor. In addition, the present invention provides a method of preventing metastasis to secondary loci or growth of existing metastatic nodules.

The patient's existing immune response to the panel of antigens can be assessed by any method known to those skilled in the art. Preferably, both cellular and humoral immune responses are assessed. Exemplary methods include radioimmunoassay, ELISAs (or any other method employing an antibody against the antigen), and cellular proliferation responses.

The strategy presented above advantageously relies on pre-existing immunity of a cancer patient. Alternatively, the present invention can be carried out by inducing immunity to an artificial cancer cell antigen to which the patient has not previously been exposed. However, cancer patients are generally immunosuppressed, and it is preferable to rely on an existing immune response rather than inducing a primary immune response to an artificial cancer cell antigen.

As a further alternative, vaccination with an artificial cancer antigen can be used as a prophylactic to prevent cancer as described in more detail in Section C below.

The pre-existing immunity can arise from vaccination (e.g., childhood vaccination programs) or from natural exposure to the antigen. Exemplary antigens are infectious disease antigens, including but not limited to, influenza antigens, polio antigens, herpes antigens (e.g., CMV, EBV, HSV), mumps antigens, measles antigens, rubella antigens, diphtheria toxin or other diphtheria antigens, pertussis antigens, hepatitis (e.g., hepatitis A and hepatitis B) antigens, or any other vaccine antigen or other wide-spread antigen to which a substantial portion of the population has been exposed. Optionally, and preferably, the subject is given a booster vaccination against the artificial antigen prior to introduction of the modified cells into the subject, as described in more detail in Section B below.

Any suitable vaccine and method of vaccination (i.e., immunization) known in the art may be employed in carrying out the present invention, as long as an active immune response against the antigen is elicited. Additionally, when administered according to the present invention, the artificial cancer cell antigen should be able to induce an active and protective immune response against unmodified cancer cells. Exemplary vaccination methods include, but are not limited to, "naked DNA" vaccines, viral and bacterial vector vaccines, liposome associated antigen vaccines, and peptide vaccines. Vaccines may be live vaccines, attenuated vaccines, killed vaccines, or subunit vaccines. Methods of vaccinating animals and humans against immunogens are well-known in the art. See, e.g., S. Crowe et al., *Infections of the Immune System*, in Basic and Clinical Immunology, 697–715 (D. P. Stites & A. I. Terr, eds., $7^{th}$ ed. 1991).

Any suitable bacterial or virus vector may be used. Preferred vaccination methods employ RNA virus vectors (e.g., negative-strand RNA virus vectors and positive-strand RNA virus vectors), more preferably, positive-strand RNA virus vectors (e.g., alphavirus vectors, retrovirus vectors, adenovirus vectors, pox-virus vectors, e.g., vaccinia vectors). Even more preferred are alphavirus vectors, yet more preferred are VEE vectors. Also preferred are alphavirus and VEE replicon particle vectors (as described below in Section E). Also preferred are alphavirus vectors in which the nucleotide sequence encoding the antigen is operably associated with an alphavirus 26S subgenomic promoter.

B. The Use of Vaccination to Boost the Patient's Pre-Existing Immunity to an Artificial Tumor Antigen.

In treating a cancer patient using pre-existing immunity as described above, preferred are methods wherein the cancer patient is given a booster immunization with the selected artificial cancer cell antigen(s) prior to inoculation of the modified cancer cells expressing the-artificial antigen. More preferably, the patient is given at least two boosters against the selected antigen(s). The booster may be given before or after the detection of cancer in the subject. Boosters may be administered before or after inoculation of the modified cancer cells into the patient. Typically, multiple booster inoculations will be spaced three, four, five, six, seven, eight, or more, weeks apart. Preferably, the boosters are spaced one to two months apart.

In preferred embodiments of the invention, the cancer patient's pre-existing immune response to an artificial cancer cell antigen is boosted by vaccination with an alphavirus vector expressing an artificial cancer cell antigen. More preferably, the alphavirus replicon vector is a VEE vector. More preferred are propagation-defective alphavirus and VEE replicon particle vectors. Replicon vectors are described in U.S. Pat. No. 5,792,462 to Johnston et al., co-pending U.S. application Ser. No. 09/122,286, and co-pending U.S. application Ser. No. 08/981,159, the disclosures of which are incorporated herein by reference in their entirety. Alphaviruses and replicon vectors are described in more detail below in Section E.

Vaccination can be by any means known in the art, as described above, but is preferably by parenteral routes (e.g., subcutaneous, intracerebral, intradermal, intramuscular, intravenous, intraarticular), most preferably by subcutaneous injection. The dose of virus is not critical as long as it is sufficient to induce an active immune response to the expressed antigen. Typically, $10^6$ to $10^8$ infectious units of virus are inoculated per vaccination. Preferably, the subject is vaccinated at least twice, with the inoculations being spaced one to two months apart.

C. The Use of Vaccination to Create an Immune Response to an Artificial Cancer Cell Antigen.

In an alternate embodiment, the present invention is used to induce an immune response to an artificial cancer cell antigen(s), including artificial tumor antigen(s). In other words, this embodiment does not rely on a pre-existing immune response.

This embodiment may be practiced prior to or following the detection of cancer in a subject. Vaccination may be carried out by any suitable method, as described above. Preferably, alphavirus vectors, more preferably VEE vectors, each as described below, are employed to vaccinate against the artificial cancer cell antigen. More preferably alphavirus or VEE replicon vectors are used.

Vaccination with the artificial cancer cell antigen(s) can be employed to induce an immune response prior to the detection of cancer as a preventative, prophylactic measure. Such a vaccination program in children (i.e., neonates, infants, juveniles or adolescents) and/or adults creates a universal artificial cancer antigen. This type of program would establish a primary and active immune response to the artificial cancer antigen before cancer develops. When a vaccinated individual develops cancer, regardless of the specific type of cancer or the native cancer antigens present, the immune response to the artificial cancer antigen would already be in place, allowing treatment by injecting cancer cells into the patient that have been genetically modified to express the artificial cancer antigen(s). Accordingly, this embodiment of the invention provides a unique strategy for vaccination against many different forms of cancer using a universal artificial cancer antigen. A universal cancer cell antigen can be used in the prevention or treatment of any cancer regardless of the type of cancer or the native antigens present on the cancer cells.

In particular embodiments, individuals can be vaccinated against an artificial cancer cell antigen(s), preferably as a child, and then given a booster as an adult. Alternatively, children and adults, preferably only adults, may be administered periodic boosters with the vaccine (e.g., every 1, 2, 3, 5, 10, or 20 years). As a further preferred alternative, when a vaccinated individual develops cancer, he or she can be given a booster(s) against the artificial antigen after diagnosis of the cancer. Preferably, at least one of the boosters would be before introduction of modified cancer cells into the patient, as described above.

As a further alternative, vaccination against an artificial cancer cell antigen(s) can be used in patients who have already been diagnosed with cancer. The patient is vaccinated against an artificial cancer cell antigen, as described above. Cancer cells are then removed from the donor patient and modified to express the artificial antigen, as described above. When the cells are introduced into the recipient patient, the immune response to the artificial cancer cell antigen will result in an immune response to native cancer cell antigens, typically by epitope spread. This embodiment of the invention can be used both to treat primary cancers (including tumors) and/or to prevent metastasis and/or to prevent growth of metastatic nodules. Preferably, the patient is given at least one vaccine booster, either before or after introduction of modified cancer cells into the patient.

As yet a further alternative and preferred embodiment, the present invention can be carried out to vaccinate individuals at risk for developing cancer. At risk individuals include, but are not limited to, individuals with a family history of cancer, individuals who have previously been treated for cancer, individuals who have been exposed to carcinogens, individuals with a history of smoking, individuals exposed to medications or medical treatments associated with the development of cancer (e.g., estrogens or radiation therapy), individuals determined to have an increased likelihood of developing cancer by genetic testing, and individuals presenting any other clinical indicia suggesting that they have an increased likelihood of developing cancer. Alternatively stated, an at risk individual is any individual who is believed to be at a higher risk than the general population for developing cancer. The present invention can be employed to immunize at risk individuals against an artificial cancer cell antigen, so that an immune response will be in place should cancer develop.

Vaccinations and boosters may be carried out by any means known in the art, as described above. Preferably an alphavirus vector expressing an artificial cancer cell antigen, more preferably a VEE vector, yet more preferably an alphavirus or VEE replicon vector, expressing an artificial cancer cell antigen, each as described below, is employed.

D. The Use of Vaccination to Create an Immune Response to Native Cancer Antigens.

In an alternate embodiment, individuals (e.g., those who are at risk, as defined above, for developing a specific cancer) can be given preventive treatment by vaccination against specific cancer antigens. The vaccine can be used to deliver a known cancer antigen to individuals in known risk groups (e.g., for breast, ovarian, colon, lung or prostate cancers or melanoma). Vaccination may be by any suitable method known in the art, as described in more detail above.

In a preferred embodiment, alphavirus vectors, preferably VEE vectors, more preferably alphavirus and VEE replicon vectors, can be used to induce an immune response to a specific cancer antigen in cancer patients. Alphavirus replicon vectors, and in particular VEE replicons, produce a stronger and more comprehensive immune response than do conventional vaccination methods. Accordingly, alphavirus vectors can successfully vaccinate against native cancer and tumor cell antigens where other vaccination methods have failed. By a comprehensive immune response, it is meant that vaccination with alphavirus replicon vectors, in particular VEE replicon vectors, induces an advantageous balance of both cellular and humoral immune responses. Thus, alphavirus vectors, preferably VEE vectors, can be used to induce an immune response against a cancer cell antigen which fails to induce an effective immune response, although already present in the cancer cells. Such post-diagnosis vaccination programs can be used to treat the primary cancer and/or to prevent metastasis and/or to prevent growth of metastatic nodules.

As a further alternative, vaccination with alphavirus vectors can be used to treat existing cancers. Subjects that have been diagnosed as having cancer can be immunized with an alphavirus vector carrying a nucleotide sequence encoding a specific cancer cell antigen (preferably, a cell-surface cancer antigen). Preferably, the nucleotide sequence encoding the specific cancer cell antigen is operably associated with a strong promoter, e.g., an alphavirus subgenomic 26S promoter. Vaccination against the native cancer cell antigen results in an immune response against the cancer cells bearing the antigen.

Any native cancer cell antigen can be employed according to the present invention. Preferred are native cancer antigens that are expressed on the surface of the cancer cell. Exemplary native cancer cell antigens for specific breast cancers are the HER2 and BRCA1 antigens. Other illustrative cancer and tumor cell antigens are described in S. A. Rosenberg ((1999) *Immunity* 10:281–87) and include, but are note limited to: MART-1/MelanA, gp100, tyrosinase, TRP-1, TRP-2, MAGE-1, MAGE-3, GAGE-1/2, BAGE, RAGE, NY-ESO-1, CDK-4, β-catenin, MUM-1, Caspase-8, KIAA0205, HPVE7, SART-1, PRAME, and p15 antigens.

E. Alphaviruses and Alphavirus Replicon Vectors.

The present invention is preferably, and advantageously, employed using alphavirus vaccines, more preferably alphavirus replicon vaccines. Alphavirus and replicon vectors are described in U.S. Pat. No. 5,792,462 to Johnston et al., copending U.S. application Ser. No. 09/122,286, co-pending U.S. application Ser. No. 08/981,159, U.S. Pat. No. 5,814,482 to Dubensky et al., U.S. Pat. No. 5,843,723 to Dubensky et al., U.S. Pat. No. 5,789,245 to Dubensky et al., U.S. Pat. No. 5,739,026 to Garoff et al., the disclosures of which are incorporated herein by reference in their entirety.

Alphavirus replicon vaccines, and in particular VEE replicon vaccines, elicit a strong host response to immunogen. While not wishing to be held to any particular theory of the invention, it appears that alphavirus replicon vectors induce a more balanced and comprehensive immune response (i.e., cellular and humoral immunity) than do conventional vaccination methods. Moreover, it appears that alphavirus vaccines induce an strong immune response, in part, because they directly infect and replicate within dendritic cells. The resulting presentation of antigen to the immune system induces a strong immune response. The alphavirus 26S subgenomic promoter also appears to give high level of expression of a heterologous nucleic acid encoding antigen. VEE replicon vaccines are able to induce an immune response in recipient animals greater than that seen in animals actually infected with the corresponding infectious organism or virus.

The term "alphavirus" has its conventional meaning in the art, and includes the various species of alphaviruses such as Eastern Equine Encephalitis virus (EEE), Venezuelan Equine Encephalitis virus (VEE), Everglades virus, Mucambo virus, Pixuna virus, Western Encephalitis virus (WEE), Sindbis virus, South African Arbovirus No. 86 (S.A.AR86), Girdwood S.A. virus, Ockelbo virus, Semliki Forest virus, Middelburg virus, Chikungunya virus, O'Nyong-Nyong virus, Ross River virus, Barmah Forest virus, Getah virus, Sagiyama virus, Bebaru virus, Mayaro virus, Una virus, Aura virus, Whataroa virus, Babanki virus, Kyziagach virus, Highlands J virus, Fort Morgan virus, Ndumu virus, Buggy Creek virus, and any other virus classified by the International Committee on Taxonomy of Viruses (ICTV) as an alphavirus. The preferred alphavirus for use in the present invention is VEE.

An "Old World alphavirus" is a virus that is primarily distributed throughout the Old World. Alternately stated, an Old World alphavirus is a virus that is primarily distributed throughout Africa, Asia, Australia and New Zealand, or Europe. Exemplary Old World viruses include SF group alphaviruses and SIN group alphaviruses. SF group alphaviruses include Semliki Forest virus, Middelburg virus, Chikungunya virus, O'Nyong-Nyong virus, Ross River virus, Barmah Forest virus, Getah virus, Sagiyama virus, Bebaru virus, Mayaro virus, and Una virus. SIN group alphaviruses include Sindbis virus, South African Arbovirus No. 86, Ockelbo virus, Girdwood S.A. virus, Aura virus, Whataroa virus, Babanki virus, and Kyzylagach virus.

Preferred are alphaviruses including attenuating mutations. The phrases "attenuating mutation" and "attenuating amino acid," as used herein, mean a nucleotide sequence containing a mutation, or an amino acid encoded by a nucleotide sequence containing a mutation, which mutation results in a decreased probability of causing disease in its host (i.e., a loss of virulence), in accordance with standard terminology in the art, whether the mutation be a substitution mutation or an in-frame deletion mutation. See; e.g., B. Davis et al., MICROBIOLOGY 132 (3d ed. 1980). The phrase "attenuating mutation" excludes mutations or combinations of mutations which would be lethal to the virus.

Appropriate attenuating mutations will be dependent upon the alphavirus used. Suitable attenuating mutations within the alphavirus genome will be known to those skilled in the art. Exemplary attenuating mutations include, but are not limited to, those described in U.S. Pat. No. 5,505,947 to Johnston et al., U.S. Pat. No. 5,185,440 to Johnston et al., U.S. Pat. No. 5,643,576 to Davis et al., U.S. Pat. No. 5,792,462 to Johnston et al., and U.S. Pat. No. 5,639,650 to Johnston et al., the disclosures of which are incorporated herein in their entirety by reference.

When the alphavirus capsid is from VEE, suitable attenuating mutations may be selected from the group consisting of codons at E2 amino acid position 76 which specify an attenuating amino acid, preferably lysine, arginine, or histidine as E2 amino acid 76; codons at E2 amino acid position 120 which specify an attenuating amino acid, preferably lysine as E2 amino acid 120; codons at E2 amino acid position 209 which specify an attenuating amino acid, preferably lysine, arginine or histidine as E2 amino acid 209; codons at E1 amino acid 272 which specify an attenuating amino acid, preferably threonine or serine as E1 amino acid 272; codons at E1 amino acid 81 which specify an attenuating amino acid, preferably isoleucine or leucine as E1 amino acid 81; codons at E1 amino acid 253 which specify an attenuating amino acid, preferably serine or threonine as E1 amino acid 253; or the deletion of E3 amino acids 56–69, or a combination of the deletion of E3 amino acids 56–59 together with codons at E1 amino acid 253 which specify an attenuating mutation, as provided above.

When the alphavirus is the South African Arbovirus No. 86 (S.A.AR86), exemplary attenuating mutations in the structural and non-structural proteins include, but are not limited to, codons at nsP1 amino acid position 538 which specify an attenuating amino acid, preferably isoleucine as nsP1 amino acid 538; codons at E2 amino acid position 304 which specify an attenuating amino acid, preferably threonine as E2 amino acid 304; codons at E2 amino acid position 314 which specify an attenuating amino acid, preferably lysine as E2 amino acid 314; codons at E2 amino acid 372 which specify an attenuating amino acid, preferably leucine, at E2 amino acid residue 372; codons at E2 amino acid position 376 which specify an attenuating amino acid, preferably alanine as E2 amino acid 376; in combination, codons at E2 amino acid residues 304, 314, 372 and 376 which specify attenuating amino acids, as described above; codons at nsP2 amino acid position 96 which specify an attenuating amino acid, preferably glycine as nsP2 amino acid 96; and codons at nsP2 amino acid position 372 which specify an attenuating amino acid, preferably valine as nsP2 amino acid 372; in combination, codons at nsP2 amino acid residues 96 and 372 which encode attenuating amino acids at nsP2 amino acid residues 96 and 372, as described above; codons at nsP2 amino acid-residue 529-which specify an attenuating amino acid, preferably leucine, at nsP2 amino acid residue 529; codons at nsP2 amino acid residue 571 which specify an attenuating amino acid, preferably asparagine, at nsP2 amino acid residue 571; codons at nsP2 amino acid residue 682 which specify an attenuating amino acid, preferably arginine, at nsP2 amino acid residue 682; codons at nsP2 amino acid residue 804 which specify an attenuating amino acid, preferably arginine, at nsP2 amino acid residue 804; codons at nsP3 amino acid residue 22 which specify an attenuating amino acid, preferably arginine, at nsP3 amino acid residue 22; and in combination, codons at nsP2 amino acid residues 529, 571, 682 and 804 and at nsP3 amino acid residue 22 which specify attenuating amino acids, as described above.

Also preferred are alphavirus vectors in which there is a mutation in the capsid protease that ablates the autoprotease activity of the capsid and results, therefore, in nonviable virus. Capsid mutations that reduce or ablate the capsid autoprotease activity of the alphavirus capsid are known in the art and are described in U.S. Pat. No. 5,792,462 to Johnston et al., co-pending U.S. application Ser. No. 09/122, 286 and co-pending U.S. application Ser. No. 08/981,159.

Attenuating mutations may be introduced into the alphavirus RNA by performing site-directed mutagenesis on the cDNA which encodes the RNA, in accordance with known procedures. See, Kunkel, *Proc. Natl. Acad. Sci. USA* 82, 488 (1985), the disclosure of which is incorporated herein by reference in its entirety. Alternatively, mutations may be introduced into the RNA by replacement of homologous restriction fragments in the cDNA which encodes for the RNA, in accordance with known procedures.

It is also desirable to employ an alphavirus vector that encodes two or more (e.g., two, three, four, five, etc.) heterologous nucleic acid sequences, preferably each encoding an antigen according to the present invention. Each heterologous nucleic acid sequence will typically be operably associated with a promoter. Alternatively, an internal ribosome entry site (IRES) sequence(s) can be placed downstream of a promoter and upstream of the heterologous nucleic acid sequence(s). The heterologous nucleic acid sequences can be associated with a constitutive or inducible promoter. The alphavirus 26S subgenomic promoter is preferred, with the VEE 26S subgenomic promoter being most preferred.

While the present invention has been described with respect to the treatment of cancer, it will be appreciated by those skilled in the art that in addition to the treatment of cancer, the present invention can be carried out to treat any type of undesired cell proliferation, as well as psoriasis.

The following examples are provided to illustrate the present invention, and should not be construed as limiting thereof.

EXAMPLE 1

Live virus vaccines: Propagation incompetent, VEE replicon vectors (VRP) previously described (P. Pushko et al., (1998) *Virology* 239:389–401) were used in these studies to deliver either an artificial tumor antigen, hemagglutinin (HA), from the influenza virus (PR/8/34, type H1N1) (P. Pushko et al., (1998) *Virology* 239:389–401) or an irrelevant antigen, SIV matrix/capsid, (M/C) (N. L. Davis et al., (1999) *Proc. Natl. Acad. Sci. USA*, submitted). Specifically, The HA or M/C gene were cloned into the VEE replicon expression vector behind the 26S subgenomic promoter, replacing the structural genes. To minimize the possibility of full length recombinant virus arising during the replicon particle packaging, the structural genes were provided in trans by two separate helper vectors, one expressing VEE capsid and the other expressing the VEE glycoprotein genes. Electroporation of RNA transcripts from all three vectors into baby hamster kidney cells (BHK) resulted in the production of infectious VEE replicon particles (VRP) which contain only the replicon expression vector genome. These particles can undergo only one round of infection during which the heterologous gene is expressed at high levels. To safeguard against the possibility that pathogenic, propagation competent particles might arise during the VRP packaging process, replicon particles were packaged using a glycoprotein helper vector that contained an attenuating mutation (V3014; E2 209 Glu→Lys; N. L. Davis et al., (1991) *Virology* 183:20–31). VRP were prepared as previously described and purified over a sucrose cushion (P. Pushko et al., (1998) *Virology* 239:389–401).

EXAMPLE 2

The gene for the Influenza hemagglutinin Puerto Rico 8 (APR8) was excised from the VRep construct using HindIII. It was cloned into pBluescript II SK-(Stratagene) at the HindIII site such that the 5' end of the gene was on the SalI side of the polylinker (HA PR8-SK). The HA PR8 gene was excised from this construct using SalI and BamHI and cloned into the pH-beta vector (P. Gunning et al., (1987) *Proc. Natl. Acad. Sci U.S.A.* 84.483.1 at the same sites (HA PR8-pH-beta). This construct drives expression of the introduced gene with the β-actin promoter and contains the gene coding for geneticin resistance.

The LINE1 mouse lung carcinoma has been described previously. B. A. Pulaski et al., (1993) *Cancer Res.* 53:2112. HA PR8-pHb was transfected into LINE1 cells via calcium phosphate precipitation as previously described. B. K. Martin et al., (1997) *Immunity* 6:591. Forty hours after transfection the cells were split 1:20 into media containing geneticin (Sigma, 800 mg/ml). Thereafter, the cells were split before they became confluent, until all cells on a mock transfected plate had died. Cells in this polyclonal pool were cloned by limiting dilution (at 0.2 cells per wells). Clones arising after limiting dilution were tested for HA expression by FACS analysis using a rabbit anti-HA polyclonal antiserum. Cells were incubated in anti-HA antiserum (1:100) in PBS for 30 minutes. Cells were washed two times in PBS followed by incubation in goat anti-rabbit IgG FITC (Pharmingen) for 20 minutes. Cells were washed three times in PBS and then analyzed on the Becton-Dickinson FACScan. In order to determine the stability of the HA expression, cells that were identified as being positive for HA expression were cultured in media without geneticin for three weeks. These clones were then analyzed by FACS for HA expression after this period as described above. One clone maintained high, stable HA expression, even in the absence of geneticin selection. This clone was designated LINE1-HA 2A9. This clone was used in subsequent mouse experiments.

EXAMPLE 3

Mice: Three groups of 8 BALBC 7–8 week old female mice (Jackson Labs) were inoculated with either $5\times10^5$ infectious units (IU) of either V3014-HA VRP, V3014–M/C VRP or diluent (phosphate buffered saline with 1% donor calf serum), subcutaneously in the rear footpad. Mice were boosted three weeks later by the same protocol, and three weeks following were inoculated intramuscularly (im) in the same calf with either $10^3$ LINE1 tumor cells or LINE1 cells expressing HA (LINE1-HA). The growth of the tumor was monitored by comparison of right and left calf diameter. Animals were sacrificed when the tumor diameter exceeded 0.5 inches.

Sections of tumor and normal muscle were fixed in 4% paraformaldehyde and frozen sections were immunostained with antiserum to flu type H1N1 (kindly provided by R. Webster, St. Jude's Children Hospital, Memphis, Tenn.), visualized using an anti-rabbit-HRP second antibody, and counter-stained with hematoxylin.

EXAMPLE 4

Since VEE specifically targets DC and there is intense interest in these cells for tumor immunotherapy, we hypothesized that VEE would be a good candidate to stimulate tumor immunity in vivo. We have used this technology to protect mice against a poorly immunogenic lung carcinoma, LINE1 (B. K. Martin et al., (1997) *Immunity* 6:591) that was molecularly engineered to express the influenza hemagglutinin gene (HA) as a model tumor antigen.

Figure 1:
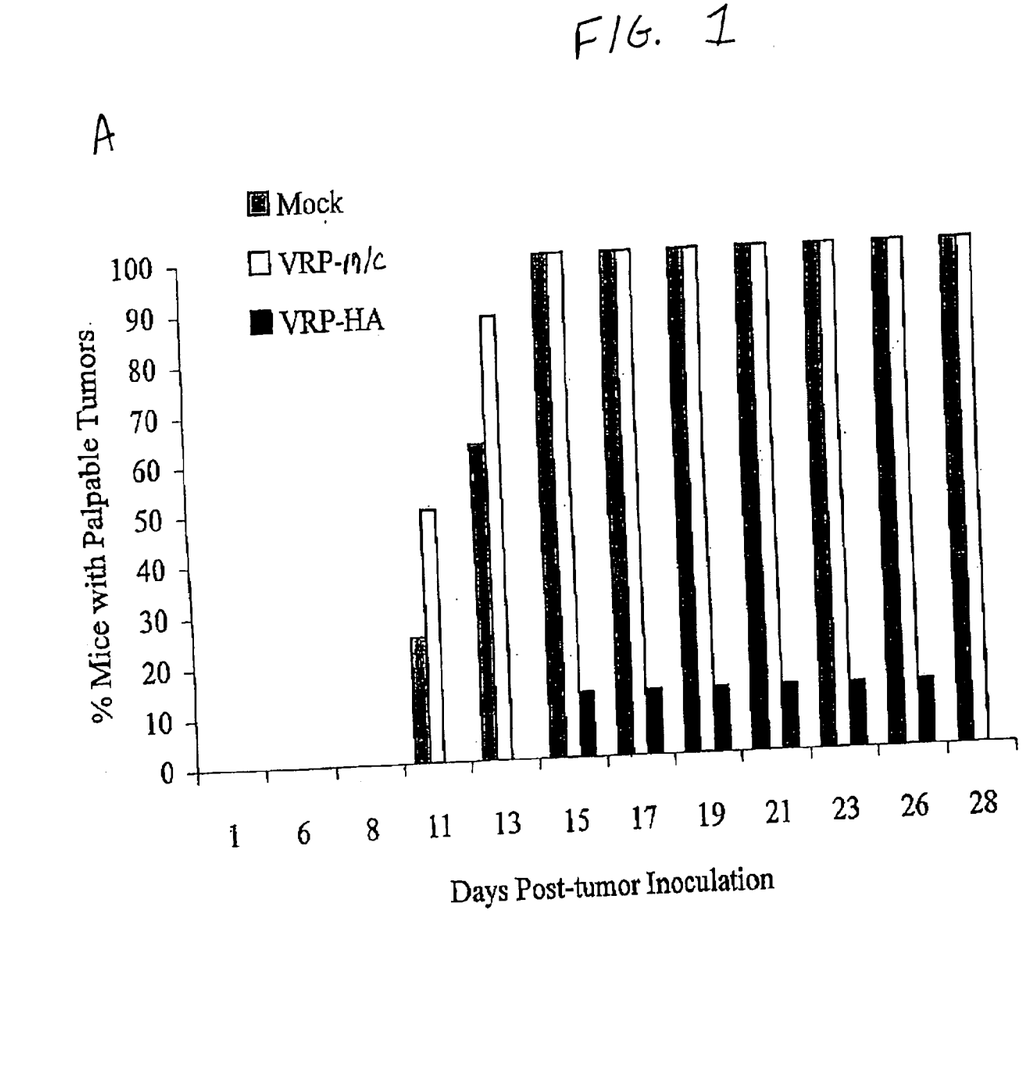

LINE1 cells were engineered to express HA on the cell surface by transfection of a plasmid encoding the HA gene under control of the actin promoter and containing the gene for G418 resistance as described above in Example 2. LINE1-HA clones were screened for stable expression of HA by FACS analysis. One clone was selected based on high, stable expression of HA in the absence of G418 drug selection (data not shown). Mice inoculated with $10^3$ LINE1-HA cells intramuscularly (im) in calf developed palpable nodules by day 11 post-inoculation (pi). These tumors grew progressively and growth was readily monitored by external caliper measurement of the calf (see FIG. 1, panels A and B). Maintenance of HA expression was confirmed by immunohistochemical staining in tumors that had reached the maximum allowed size (data not shown).

Propagation incompetent VRPs, previously described (P. Pushko et al., (1998) *Virology* 239:389–401), were used to deliver either the model tumor antigen, HA, or an irrelevant control antigen, SIV matrix/capsid (M/C). While these viral particles that lack VEE structural genes are fully infectious, they and can undergo only one round of infection, during which the heterologous gene is expressed at high levels. To safeguard against the possibility that pathogenic, propagation competent particles might arise during the VRP packaging process, replicon particles were packaged using a glycoprotein helper vector that contained an attenuating mutation (V3014; E2 209 Glu→Lys; N. L. Davis et al., (1991) *Virology* 183:20–31).

Three groups of 8 BALBC mice were inoculated with $1\times10^6$ infectious units (IU) of either VRP-HA, VRP-M/C or diluent (phosphate buffered saline with 1% donor calf serum), subcutaneously (sc) in the rear footpad. Mice were boosted three weeks later by the same protocol, and three weeks following were inoculated im in the same calf with $10^3$ LINE1-HA tumor cells. The growth of the tumor was monitored both by manual palpation and caliper measurements of right and left calf diameters. Vaccination of mice with VRP-HA significantly inhibited the incidence of tumor establishment (FIG. 1). Palpable nodules were first detected by day 11 in 25% and 50% of the mice in the mock and VRP-M/C control groups respectively. By day 15 one hundred percent of mice in both control groups were positive for palpable tumors. These tumors continued to grow and increase in size to 0.5 inches in diameter, at which point mice were sacrificed (FIG. 1A). In contrast, only one out of eight mice vaccinated with VRP-HA developed a palpable nodule by day fifteen. However, this nodule never grew above 0.2 inches in diameter and was resolved to be undetectable by palpation at day 28. The average calf measurement in the VRP-HA group was significantly less than that of both control groups starting at day 11 ($p<0.01$) in spite of the presence of a detectable mass in one mouse (FIG. 1).

EXAMPLE 5

To test the effect of VRP-HA on tumor regression, 7 mice from the negative control groups from Example 3 and Example 4, above, with tumors under 0.3 inches in diameter were immunized with $10^6$ IU of VRP-HA on day 31 post-LINE1-HA inoculation.

Figure 2:
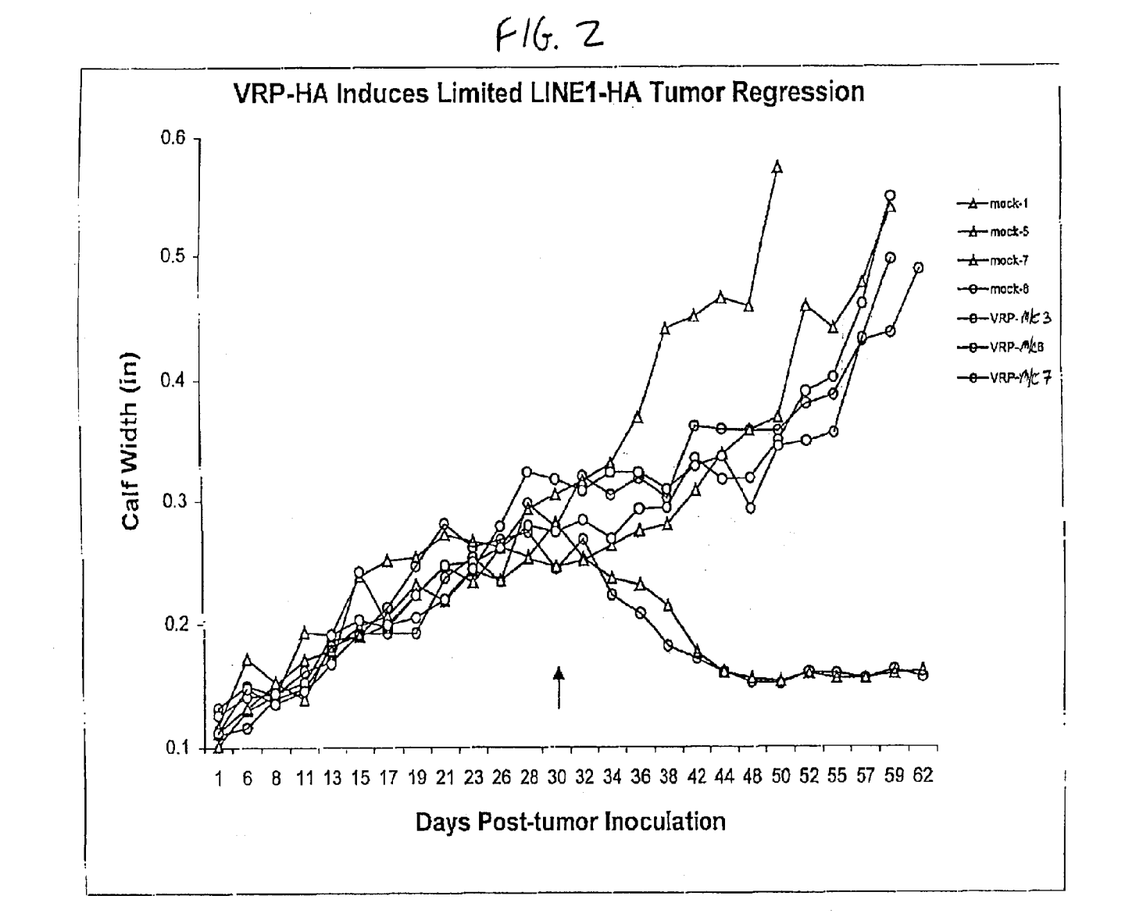

Treatment of mice from the negative control group with tumors less than 0.3 inches in diameter with VRP-HA resulted in complete regression of tumors in two of seven mice (FIG. 2). No similar regression in untreated mice was observed.

EXAMPLE 6

To determine whether anti-LINE1-HA immunity induced by immunization with VRP-HA could now confer cross-protection to LINE1 tumor cells not expressing HA, mice resistant to LINE1-HA tumors were inoculated on day 48 (post-LINE1-HA inoculation) with LINE1 tumor cells not expressing HA. Eight mice from the group pre-immunized with VRP-HA before LINE1-HA inoculation and which never developed tumors (Example 3 and Example 4, above), two mice from the negative control group whose tumors regressed after receiving VRP-HA (Example 5), and four naive mice which had never been immunized with either VRP-HA or LINE1-HA were injected im with $10^3$ LINE1 cells in either the left or right calf and tumor growth was monitored as described above.

Figure 3:
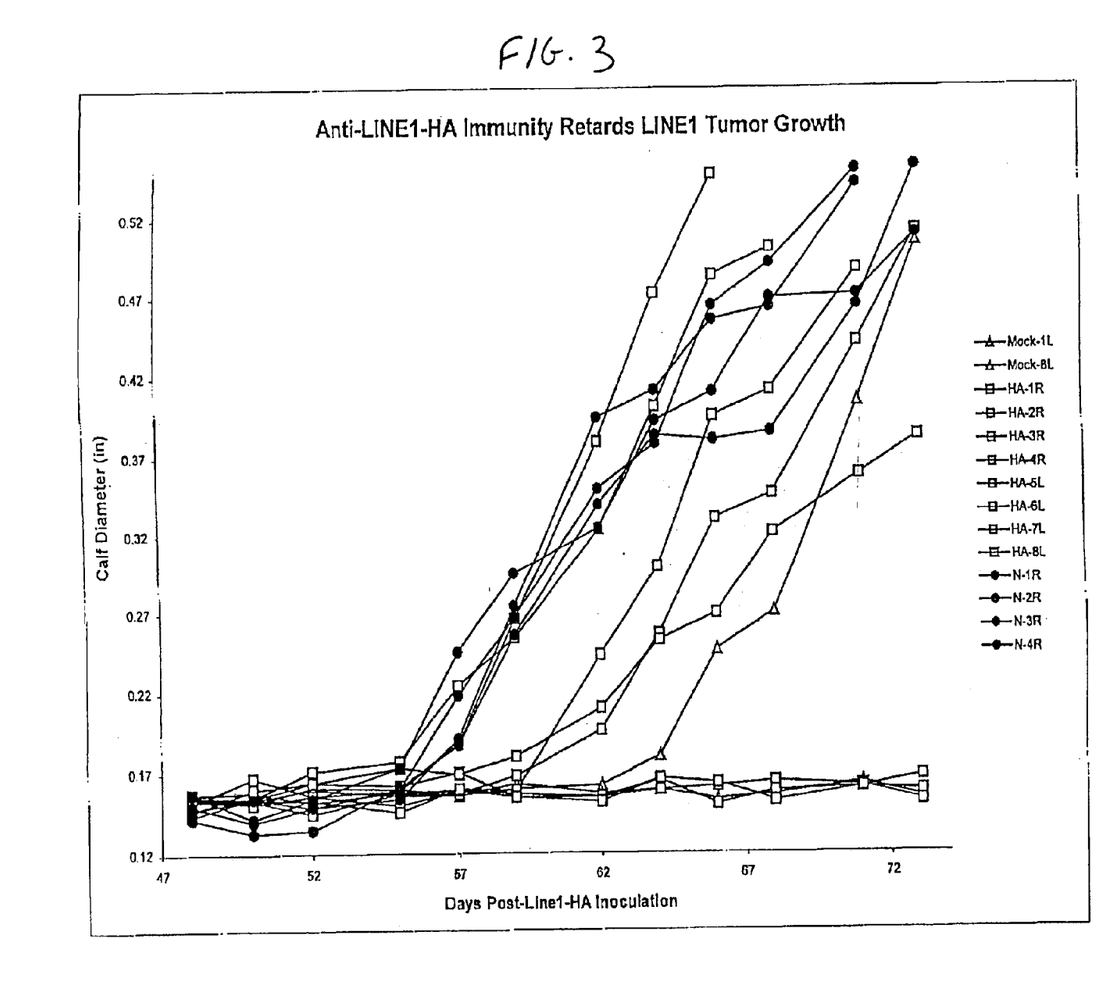
Figure 4:
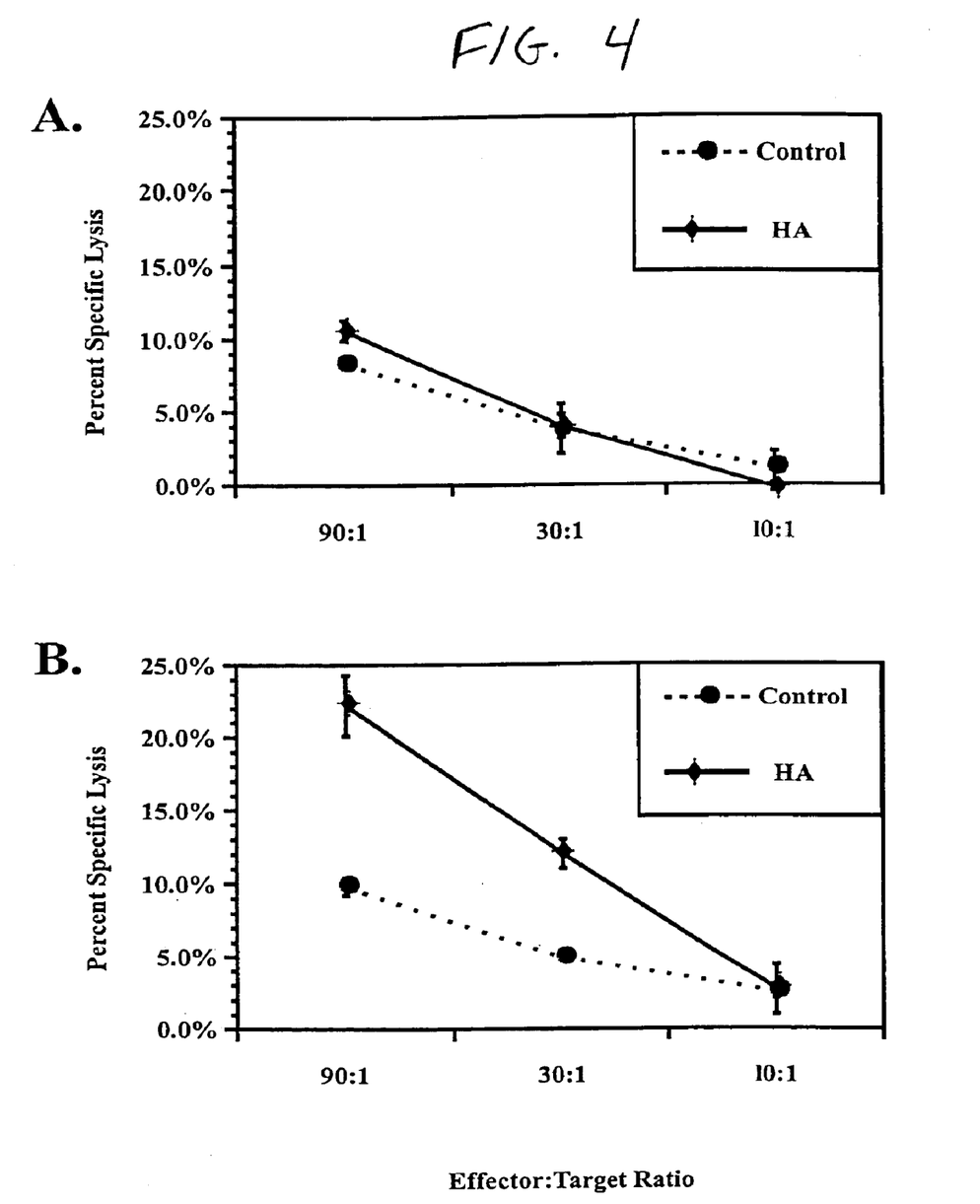
FIGS. 4A and 4B represent the results of a study demonstrating that VRP-HA vaccinated mice develop HA-specific CTL activity. Mice were vaccinated with either VRP-HA or VRP-M/C. Three weeks after the second injection, splenocytes were harvested and then cultured for seven days in the presence of irradiated 4T1 cells ($H-2^d$) or HA expressing 4T1 cells and interleukin-2. The resulting cells were tested for CTL activity against either 4T1 cells or 4T1 cells expressing HA. Activity is expressed as percent specific lysis. Closed circles represent CTL activity against parental 4T1 cells; closed diamonds represent CTL activity against 4T1 cells expressing HA. Panel A, splenocyte CTL activity from VRP-M/C vaccinated mice; Panel B, splenocyte CTL activity from VRP-HA vaccinated mice.

Immunity to LINE 1-HA tumors significantly delayed or prevented LINE1 tumor growth in 8 out of 10 mice tested (FIG. 3). While all four naive mice rapidly developed LINE1 tumors, only two of the ten LINE1-HA immune mice developed LINE1 tumors with similar kinetics. While four immune mice had a significant delay in the onset of LINE1 tumor growth, four mice were completely resistant to tumor establishment. There was no correlation between delay in tumor growth and inoculation of LINE1 cells in the right or left calf.

Half of the mice injected with LINE1 cells were injected in the left calf, and half were injected in the right calf. The original inoculation with VPR-HA (Example 2) was in the left calf, and this experimental design was employed to determine whether the protective effects of the first set of inoculations with VRP-HA would be local or systemic effects. There was no difference in tumor growth between mice injected with LINE1 cells in either the left or right calves. These results indicate that the immunity provided by VRP-HA inoculation against LINE1 cells was systemic in effect and not limited to the area around the original site of inoculation.

EXAMPLE 7

Although previous studies have demonstrated that mice inoculated with VRP expressing heterologous antigens, including HA, develop very high antibody titers to those antigens (P. Pushko et al., (1998) *Virology* 239:389–401; N. L. Davis et al., (1999) *Proc. Natl. Acad. Sci. USA*, submitted), less is known about the capacity of VRP immunizations to stimulate CTL activity in mice. Induction of CTL is very important for vigorous antitumor immunity, therefore we investigated that capacity of VEE inoculation to induce this response.

Figure 5:
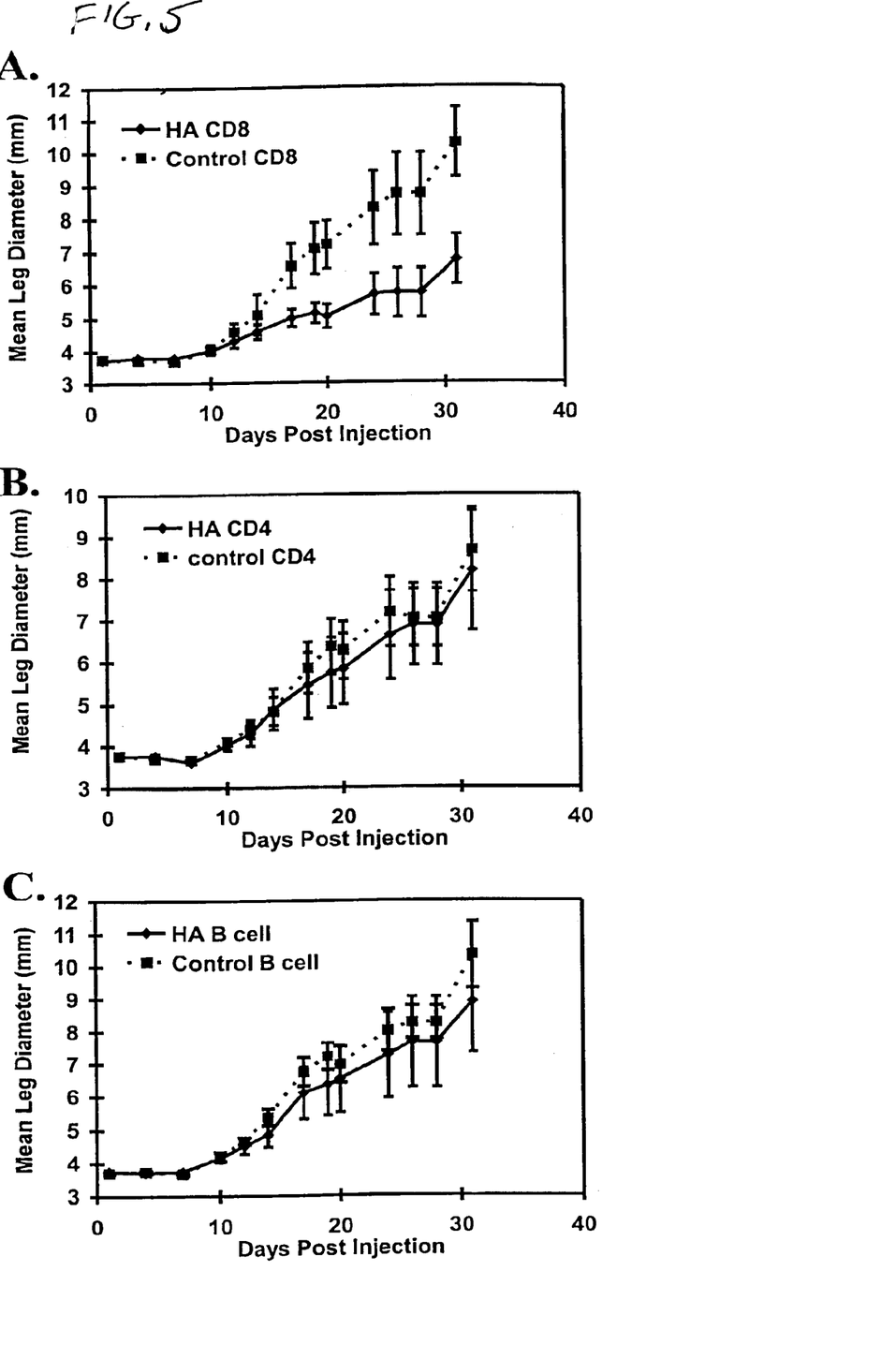

Mice were vaccinated with VRP-HA or VRP-M/C as above and whole splenocytes were removed, expanded in vitro and tested for HA-specific CTL activity. Mice vaccinated with VRP-HA developed significant HA-specific CTL activity (FIG. 4, Panel B), compared to mice receiving VRP-M/C (FIG. 4, Panel A), demonstrating that this protocol can successfully generate HA-specific CTLs. Although, we had shown that VRP-HA inoculation could generate CTL, it was not known whether this cellular population are the effectors responsible for tumor protection. To determine if the CTL compartment was responsible for antitumor immunity, mice were vaccinated with either VRP-HA or VRP-M/C as above with an additional boost. Splenocytes were fractionated into $CD4^+$ T cells, $CD8^+$ T cells and flow-through cells (B-cells and other splenocytes) and transferred intravenously to naive recipient mice. Forty-eight hours later recipient mice and naive mice were challenged with LINE1-HA tumor cells as described previously. Mice that had received VRP-HA immune $CD8^+$ T cells had significantly smaller tumors than mice receiving either $CD8^+$ T cells from mice vaccinated with VRP-M/C ($p=0.034$ at day 31) (FIG. 5). Mice injected with CD4+ T cells or flow-through cells from HA inoculated mice did not have significantly different growth from mice injected with the same cells from VRP-M/C mice. These results along with the ability to demonstrate significant HA-specific CTL activity suggest that $CD8^+$ CTL activity protects mice against tumor growth. However, the protection achieved with CD8+ T cell transfer was inferior to that developed with viral inoculation in that all mice did eventually develop tumors. This suggests that other cells are required for full protection. This could include helper T cells, B cells and/or dendritic cells.

The data presented herein demonstrate for the first time that a virus specifically targeted to dendritic cells can be an efficient in vivo vector system for delivery of tumor antigen genes to DC. A number of viruses, including retrovirus, adenovirus and vaccinia have been shown to infect DC in vitro (J. M. Specht et al., (1997) *J. Experimental Medicine* 186:1213–1221; P. Brossart et al., (1997) *J. Immunology* 158: 3270–76, M. De Veerman et al., (1999) *J. Immunology* 162:144–151) and in many cases specific infection of DC can lead to protective tumor immunity when the DC are infused back into the mice.

EXAMPLE 8

Three groups of BALBC mice are inoculated sc in the left rear foot pad with either diluent or $10^6$ IU of either VRP-HA or VRP-M/C. Mice are boosted three weeks later by the same protocol. Three weeks following the boost, mice are injected im in the left calf muscle with $10^3$ LINE1 cells. After tumors have developed, the animals are injected im in the left calf muscle with $10^3$ LINE1-HA cells, and tumor regression is monitored. VRP-HA inoculated animals show regression of LINE1 tumors following injection of LINE1-HA cells. The groups of animals inoculated with diluent or VRP-M/C show no significant tumor regression.

EXAMPLE 9

Three groups of BALBC mice are injected im in the left calf muscle with $10^3$ LINE1 cells. After tumors have developed, the animals are inoculated sc in the left rear foot pad with either diluent or $10^6$ of either VRP-HA or VRP-M/C. Mice are boosted three weeks later by the same protocol. Three weeks following the boost, the animals are injected im in the left calf muscle with $10^3$ LINE1-HA cells, and tumor regression is monitored. VRP-HA inoculated animals show regression of LINE1 tumors following injection of LINE1-HA cells. The groups of animals inoculated with diluent or VRP-M/C show no significant tumor regression.

EXAMPLE 10

Three groups of BALBC mice are inoculated sc in the left rear foot pad with either diluent or $10^6$ IU of either VRP-HA or VRP-M/C. Mice are boosted three weeks later by the same protocol. Three weeks following the boost, mice are injected im in the left calf muscle with $10^3$ melanoma cells. After tumors have developed, the animals are injected im in the left calf muscle with $10^3$ melanoma cells that have been engineered to express HA (or any other antigen), and tumor regression is monitored. VRP-HA inoculated animals show regression of the tumor following injection of melanoma-HA cells. The groups of animals inoculated with diluent or VRP-M/C show no significant tumor regression.

In a second study, three groups of BALBC mice are injected im in the left calf muscle with $10^3$ melanoma cells. After tumors have developed, the animals are inoculated sc in the left rear foot pad with either diluent or $10^6$ IU of either VRP-HA or VRP-M/C. Mice are boosted three weeks later by the same protocol. Three weeks following the boost, the animals are injected im in the left calf muscle with $10^3$ melanoma-HA cells, and tumor regression is monitored. VRP-HA inoculated animals show tumor regression following injection of melanoma-HA cells. The groups of animals inoculated with diluent or VRP-M/C show no significant tumor regression.

Although the foregoing invention has been described in some detail by way of illustration and example for purposes of clarity and understanding, it will be obvious that certain changes and modifications may be practiced within the scope of the appended claims and equivalents thereof.

That which is claimed is:

1. A composition comprising infectious Venezuelan Equine Encephalitis (VEE) replicon particles, wherein said VEE replicon particles comprise one or more heterologous nucleotide sequences encoding the Her2 antigen, and wherein said VEE replicon particles infect antigen-presenting cells, and further wherein said VEE replicon particles comprise one or more attenuating mutations.

2. The composition of claim 1, wherein each of said one or more heterologous nucleotide sequences is operably associated with a promoter.

3. The composition of claim 2, wherein said promoter operably associated with each of said one or more heterologous nucleotide sequences is an alphavirus 26S subgenomic promoter.

4. A pharmaceutical formulation comprising the composition of claim 1 in a pharmaceutically acceptable carrier.

5. The composition of claim 1, wherein at least one of said one or more attenuating mutations is selected from the group consisting of codons at E2 amino acid position 76 which specify an attenuating amino acid, codons at E2 amino acid position 120 which specify an attenuating amino acid, codons at E2 amino acid position 209 which specify an attenuating amino acid, codons at E1 amino acid 272 which specify an attenuating mutation, codons at E1 amino acid 81 which specify an attenuating mutation, and codons at E1 amino acid 253 which specify an attenuating mutation, and the deletion of E3 amino acids 56–59.

6. The composition of claim 1, wherein said antigen-presenting cells are dendritic cells.

* * * * *

UNITED STATES PATENT AND TRADEMARK OFFICE
CERTIFICATE OF CORRECTION

PATENT NO. : 6,844,188 B1
DATED : January 18, 2005
INVENTOR(S) : MacDonald et al.

It is certified that error appears in the above-identified patent and that said Letters Patent is hereby corrected as shown below:

<u>Title page,</u>
Item [73], Assignee, should read -- University of North Carolina at Chapel Hill, Chapel Hill, NC (US) --
Item [56], References Cited, OTHER PUBLICATIONS, should include the following references:
-- Jain, Cancer and Metastasis Reviews 9:253-266, 1990.
Osband et al. Immunology Today, 11/6:193.-195.
Gura, Science 278:1041-1042, 1997. --

Signed and Sealed this

Seventh Day of June, 2005

JON W. DUDAS
*Director of the United States Patent and Trademark Office*